United States Patent
Kohli et al.

(10) Patent No.: US 12,290,374 B2
(45) Date of Patent: May 6, 2025

(54) SYSTEM AND METHOD FOR TESTING THE EFFECTS OF ULTRAVIOLET AND VISIBLE LIGHT ON SKIN

(71) Applicant: HENRY FORD HEALTH SYSTEM, Detroit, MI (US)

(72) Inventors: Indermeet Kohli, Westland, MI (US); Iltefat H. Hamzavi, Northville, MI (US); Henry W. Lim, Grosse Pointe, MI (US); Angela Miller, Belleville, MI (US); Tasneem Mohammad, Canton, MI (US); Cynthia Nicholson, Royal Oak, MI (US); Suteeraporn Chaowattanapanit, Nakhon Ratchasima (TH)

(73) Assignee: Henry Ford Health System, Detroit, MI (US)

( * ) Notice: Subject to any disclaimer, the term of this patent is extended or adjusted under 35 U.S.C. 154(b) by 687 days.

(21) Appl. No.: 17/625,636

(22) PCT Filed: Jul. 9, 2020

(86) PCT No.: PCT/US2020/041389
§ 371 (c)(1),
(2) Date: Jan. 7, 2022

(87) PCT Pub. No.: WO2021/007420
PCT Pub. Date: Jan. 14, 2021

(65) Prior Publication Data
US 2022/0240838 A1  Aug. 4, 2022

Related U.S. Application Data

(60) Provisional application No. 62/871,897, filed on Jul. 9, 2019.

(51) Int. Cl.
*A61B 5/00* (2006.01)
*A61N 5/06* (2006.01)
(Continued)

(52) U.S. Cl.
CPC ............... *A61B 5/441* (2013.01); *A61N 5/06* (2013.01); *F21S 8/006* (2013.01); *F21V 9/02* (2013.01);
(Continued)

(58) Field of Classification Search
None
See application file for complete search history.

(56) References Cited

U.S. PATENT DOCUMENTS

2003/0228267 A1   12/2003   Aust et al.
2009/0091325 A1   4/2009    Haywood

FOREIGN PATENT DOCUMENTS

WO   0212127 A2     2/2002
WO   2018217432 A1  11/2018

OTHER PUBLICATIONS

Schalka et al. (Sunscreen protection against visible light: a new proposal for evaluation; 2012) Surg Cosmet Dermatol 2012;3(4):45-52. (Year: 2012).*

(Continued)

*Primary Examiner* — Jay B Shah
(74) *Attorney, Agent, or Firm* — Brooks Kushman P.C.

(57) ABSTRACT

A system and method for testing an effect of light exposure on a skin sample include a solar simulator arranged to administer a combination of visible light (VL) and long wavelength ultraviolet radiation (UVA1) to the skin sample. The solar simulator includes a lamp for generating a light beam and at least one customized filter for receiving the light
(Continued)

beam and emitting a VL+UVA1 spectral output having a wavelength range of 370-700 nm for irradiating the skin sample.

11 Claims, 4 Drawing Sheets

(51) Int. Cl.
*F21S 8/00* (2006.01)
*F21V 9/02* (2018.01)

(52) U.S. Cl.
CPC ... *A61B 2503/42* (2013.01); *A61N 2005/0661* (2013.01); *A61N 2005/0662* (2013.01)

(56) References Cited

OTHER PUBLICATIONS

Schalka et al. A novel method for evaluating sun visible light protection factor and pigmentation protection factor of sunscreens; Clinical, Cosmetic and Investigational Dermatology Aug. 2019:12 605-616 (Year: 2019).*

European Extended Search Report for Application No. 20837322. 5-1020, dated Jul. 31, 2023, 12 pages.
Kohli et al., "Synergistic effects of long-wavelength ultraviolet A1 and visible light on pigmentation and erytherma", British Journal of Dermatology, 2018, 178, pp. 1173-1180.
Mahmoud et al., "Impact of Long Wavelength UVA and Visible Light on Melanocompetent Skin", Journal of Investigative Dermatology, 2010, vol. 130, pp. 2092-2097.
De Argila D et al., "Study of Idiopathic, Exogenous Photodermatoses, Part II: Photobiologic Testing", Actas Dermosifiliograficas (English Edition), Elsevier, Amsterdam, NL, vol. 105, No. 3, Feb. 27, 2014, pp. 233-242.
Schott, "Schott Optical Glass 2018", Jan. 1, 2018, 147 pages.
International Search Report and Written Opinion for Application No. PCT/US2020/041389, dated Oct. 8, 2020, 9 pages.
International Preliminary Report on Patentability for Application No. PCT/US2020/041389, dated Jan. 11, 2022, 8 pages.
Kohli et al., "Synergistic effects of long-wavelength ultraviolet A1 and visible light on pigmentation and erytherma", British Journal of Dermatology, 2018, 178, pp. 1173-1180, with Supplementary Materials and Methods S1.

* cited by examiner

SYSTEM AND METHOD FOR TESTING THE EFFECTS OF ULTRAVIOLET AND VISIBLE LIGHT ON SKIN

CROSS-REFERENCE TO RELATED APPLICATIONS

This application is the U.S. national phase of PCT Application No. PCT/US2020/041389 filed Jul. 9, 2020 which claims the benefit of U.S. provisional application Ser. No. 62/871,897 filed Jul. 9, 2019, the disclosures of which are hereby incorporated in their entirety by reference herein.

TECHNICAL FIELD

Embodiments relate to a system and method for testing the effects of a combination of ultraviolet and visible light on a skin sample.

BACKGROUND

Solar radiation is known to be a major contributor to the development of skin cancer. Sun care guidelines recommended by the American Academy of Dermatology include staying in the shade when outdoors, wearing photoprotective clothing, wearing a wide-brimmed hat and sunglasses, and applying broad spectrum sunscreen with a sun protection factor of 30 or above. The sun protection factor value represents the ratio of minimal erythema dose of sunscreen-protected skin to that of unprotected skin.

To evaluate protection of sunscreens against ultraviolet A radiation, the critical wavelength method is recommended by the Food and Drug Administration in the United States. An in vitro spectrophotometer scan of the absorbance spectra of the sunscreen is performed and the area under the curve is then calculated starting at 290 nm. The wavelength at which 90% of the area under the curve occurs is called the critical wavelength. The pass/fail criteria of claiming broad-spectrum protection is 370 nm, allowing any sunscreen with a critical wavelength of 370 nm or above to claim broad-spectrum protection on its label. However, most sunscreen formulations, including those with broad spectrum, offer minimal protection in the long wavelength ultraviolet A1 (UVA1; 370-400 nm) and visible light (VL; 400-700 mm) domains.

SUMMARY

In one or more embodiments, a system for testing an effect of light exposure on a skin sample includes a solar simulator arranged to administer a combination of visible light (VL) and long wavelength ultraviolet radiation (UVA1) to the skin sample. The solar simulator includes a light source for generating a light beam, and at least one customized filter for receiving the light beam and emitting a VL+UVA1 spectral output having a wavelength range of 370-700 nm for irradiating the skin sample.

In one or more embodiments, a method for testing an effect of light exposure on a skin sample includes providing a solar simulator arranged to administer a combination of visible light (VL) and long wavelength ultraviolet radiation (UVA1) to the skin sample, the solar simulator including a light source for generating a light beam and at least one customized filter for receiving the light beam and emitting a VL+UVA1 spectral output having a wavelength range of 370-700 nm; and irradiating the skin sample with the VL+UVA1 spectral output.

In one or more embodiments, a method for testing an effect of light exposure on a skin sample includes providing a solar simulator arranged to administer a combination of visible light (VL) and long wavelength ultraviolet radiation (UVA1) to the skin sample, the solar simulator including a lamp for generating a light beam and at least one customized filter for receiving the light beam and emitting a VL+UVA1 spectral output comprising approximately 2.0% UVA1 (340-400 nm), approximately 97.3% VL (400-700 nm) and approximately 0.7% Infrared (700-1600 nm). The method further includes irradiating the skin sample with the VL+UVA1 spectral output, and evaluating the skin sample after irradiation.

In one or more embodiments, the at least one customized filter comprises a customized filter combination including a long pass filter and a customized interference filter.

In one or more embodiments, the VL+UVA1 spectral output comprises approximately 2.0% UVA1 (340-400 nm), approximately 97.3% VL (400-700 nm) and approximately 0.7% Infrared (700-1600 nm).

In one or more embodiments, approximate percentage ranges of irradiance for the VL+UVA1 spectral output are:

| Waveband (nm) | Percentage Range |
| --- | --- |
| below 370 | less than 0.0001% |
| 370-400 | 0.1-4% |
| 400-700 | 94-99.8% |
| 700-1600 or 4000 | 0.1-2% |

In one or more embodiments, approximate percentage ranges of irradiance for the VL+UVA1 spectral output are:

| Waveband (nm) | Percentage Range |
| --- | --- |
| below 370 | less than 0.0001% |
| 370-400 | 0.01-5% |
| 400-700 | 93-99.98 |
| 700-1600 or 4000 | 0.01-2% |

In one or more embodiments, a total irradiance of the VL+UVA1 spectral output is from about 40-500 mW/cm$^2$.

In one or more embodiments, a total irradiance of the VL+UVA1 spectral output is less than a factor of 2 compared to a total irradiance of sunlight.

In one or more embodiments, the effect on the skin sample includes changes in at least one of pigmentation or erythema.

In one or more embodiments, the method includes treating the skin sample with a photoprotective substance prior to irradiation.

DETAILED DESCRIPTION

Figure 1:
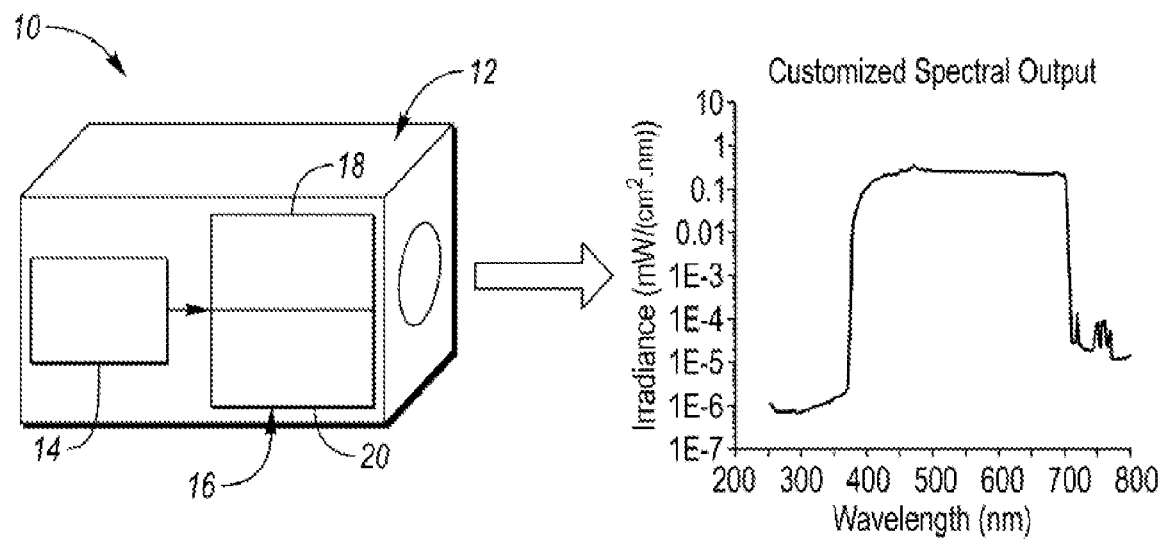
FIG. 1 is a schematic representation of a system for generating visible light (VL)+ultraviolet A1 (UVA1) irradiation including a customized filter combination used to generate a customized spectral output according to one or more embodiments.

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about". The first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

Unless indicated otherwise, all technical and scientific terms used herein have the same meaning as commonly understood by one of ordinary skill in the art to which the present disclosure belongs.

It is also to be understood that this disclosure is not limited to the specific embodiments and methods described below, as specific components and/or conditions may, of course, vary. Furthermore, the terminology used herein is used only for describing particular embodiments and is not intended to be limiting in any way.

It must also be noted that, as used in the specification and the appended claims, the singular form "a", "an," and "the" comprise plural referents unless the context clearly indicates otherwise. For example, reference to a component in the singular is intended to comprise a plurality of components. The terms "or" and "and" can be used interchangeably and can be understood to mean "and/or".

The term "comprising" is synonymous with "including," "having," "containing," or "characterized by." These terms are inclusive and open-ended and do not exclude additional, unrecited elements or method steps.

The phrase "consisting of" excludes any element, step, or ingredient not specified in the claim. When this phrase appears in a clause of the body of a claim, rather than immediately following the preamble, it limits only the element set forth in that clause; other elements are not excluded from the claim as a whole.

The phrase "consisting essentially of" limits the scope of a claim to the specified materials or steps, plus those that do not materially affect the basic and novel characteristic(s) of the claimed subject matter.

The terms "comprising", "consisting of", and "consisting essentially of" can be alternatively used. When one of these three terms is used, the presently disclosed and claimed subject matter can include the use of either of the other two terms.

Unless expressly stated to the contrary: percent, "parts of," and ratio values are by weight; the description of a group or class of materials as suitable or preferred for a given purpose in connection with the disclosure implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed.

It should also be appreciated that integer ranges explicitly include all intervening integers. For example, the integer range 1-10 explicitly includes 1, 2, 3, 4, 5, 6, 7, 8, 9, and 10. Similarly, the range 1 to 100 includes 1, 2, 3, 4 . . . 97, 98, 99, 100. Similarly, when any range is called for, intervening numbers that are increments of the difference between the upper limit and the lower limit divided by 10 can be taken as alternative upper or lower limits. For example, if the range is 1.1. to 2.1 the following numbers 1.2, 1.3, 1.4, 1.5, 1.6, 1.7, 1.8, 1.9, and 2.0 can be selected as lower or upper limits.

In the examples set forth herein, concentrations, temperature, and reaction conditions (e.g., irradiance, pressure, pH, flow rates, etc.) can be practiced with plus or minus 50 percent of the values indicated rounded to or truncated to two significant figures of the value provided in the examples. In a refinement, concentrations, temperature, and reaction conditions (e.g., irradiance, pressure, pH, flow rates, etc.) can be practiced with plus or minus 30 percent of the values indicated rounded to or truncated to two significant figures of the value provided in the examples. In another refinement, concentrations, temperature, and reaction conditions (e.g., irradiance, pressure, pH, flow rates, etc.) can be practiced with plus or minus 10 percent of the values indicated rounded to or truncated to two significant figures of the value provided in the examples.

Visible light (VL) induces multiple cutaneous effects, including dark and persistent pigmentation, erythema, DNA damage secondary to free radical production and exacerbation of photodermatoses. Sunscreen testing protocols recommended by regulatory bodies throughout the world require the use of solar simulators with spectral output in the ultraviolet (UV) domain only. However, sunlight contains VL and infrared radiation also. While a great deal of research has been performed on protection for the UV portion of the solar spectrum, there is a lack of such information un VL. Regulatory bodies throughout the world follow set methodologies to test product efficacy against the deleterious effects of UV radiation, but there are no guidelines or protocols to test for protection against VL in any country.

To address the need for protection in the VL and UVA1 domains, a system and method for testing the effects of light exposure with a combination of VL and long wavelength ultraviolet A1 (UVA1) irradiation on a skin sample are provided herein, wherein VL+UVA1 has a wavelength range of 370-700 nm. Biologic effects on the skin include, but are not limited to, changes in pigmentation and erythema. With reference to FIG. 1, the system 10 includes a solar simulator 12 (e.g., LS1000, Solar Light Company, Inc., Glenside, PA) with a light source or lamp 14, such as a xenon arc lamp, and at least one customized filter or customized filter combination 16 for irradiation purposes. In one or more embodiments, the solar simulator 12 may generate a light beam with a diameter (e.g. 15 cm) sufficient to irradiate a plurality of skin samples simultaneously. In addition, in order to be time efficient, the irradiance used during testing may be higher than natural sunlight.

The solar simulator 12 may be used to administer an irradiation dose to the skin sample. In previous testing systems, a solar simulator typically provided a spectral output of 290-400 nm, corresponding to the wavelength range of UV radiation. In one or more embodiments, the solar simulator 12 utilized herein was modified to include a customized filter combination 16 to generate the customized spectral output of VL+UVA1 irradiation. In one non-limiting example, the customized filter combination 16 may include a long pass filter 18 (e.g. GG 395/3-mm, Schott North America, Inc., Duryea, PA) and a customized interference filter 20.

Figure 2:
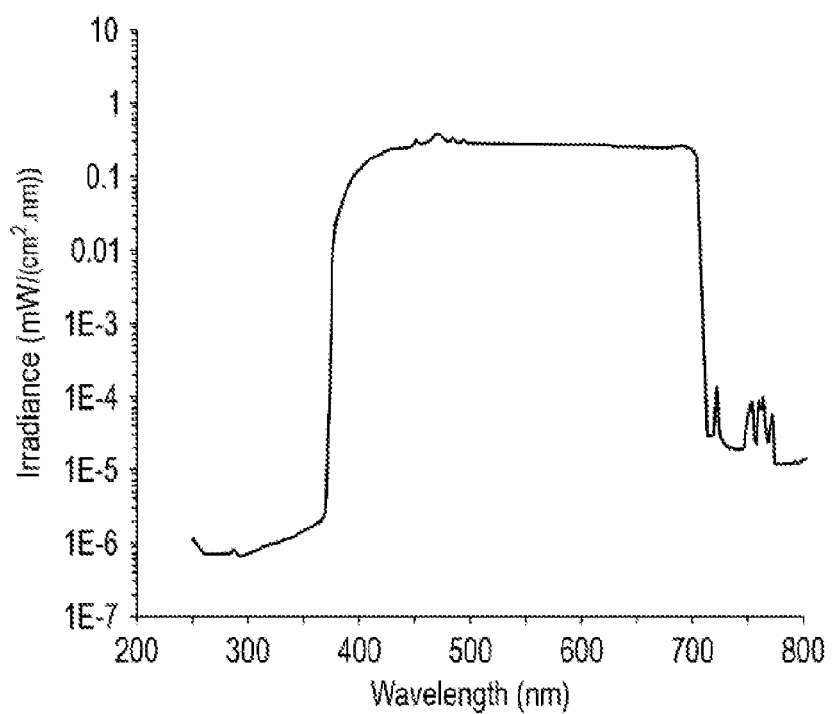
FIG. 2 is a graph of the customized spectral output according to one or more embodiments showing irradiance as a function of wavelength.

In one or more embodiments, the spectral output of the filtered light emitted from the customized interference filter 20 may include approximately 2.0% UVA1 (340-400 nm), approximately 97.3% VL (400-700 nm) and approximately 0.7% Infrared (700-1600 nm), wherein this spectral output is depicted in the graph of FIG. 2. The customized interference filter 20 was specially created to achieve this spectral output, as off-the-shelf filters do not exist in these wavebands with the specific cut-offs required to generate VL in combination with UVA1 as employed in the system and method disclosed herein.

In a non-limiting embodiment, the customized interference filter 20 may have an irradiance (mW/cm$^2$) at representative wavelengths in and around the VL+UVA1 region as follows:

| Wavelength | Irradiance |
|---|---|
| 330 | 1.06E−06 |
| 340 | 1.20E−06 |
| 350 | 1.50E−06 |
| 360 | 1.74E−06 |
| 370 | 3.64E−06 |
| 380 | 0.02747 |
| 390 | 0.07674 |
| 400 | 0.13087 |
| 410 | 0.16995 |
| 420 | 0.2113 |
| 430 | 0.22086 |
| 440 | 0.24733 |
| 450 | 0.31017 |
| 460 | 0.30651 |
| 470 | 0.37142 |
| 480 | 0.3173 |
| 490 | 0.30151 |
| 500 | 0.28952 |
| 510 | 0.2895 |
| 520 | 0.28782 |
| 530 | 0.29129 |
| 540 | 0.28813 |
| 550 | 0.2914 |
| 560 | 0.28423 |
| 570 | 0.2821 |
| 580 | 0.28098 |
| 590 | 0.27988 |
| 600 | 0.26989 |
| 610 | 0.26579 |

-continued

| Wavelength | Irradiance |
|---|---|
| 620 | 0.27094 |
| 630 | 0.26028 |
| 640 | 0.2484 |
| 650 | 0.25565 |
| 660 | 0.23897 |
| 670 | 0.24174 |
| 680 | 0.24049 |
| 690 | 0.25825 |
| 700 | 0.22423 |
| 710 | 3.08E−05 |

Of course, other irradiance values for the above wavelengths are also fully contemplated. More generally, the table below provides approximate percentage ranges of irradiance within different wavebands according to one or more embodiments for VL+UVA1 spectral output for the system and method disclosed herein:

| Waveband (nm) | Percentage Range |
|---|---|
| below 370 | less than 0.0001% |
| 370-400 | 0.1-4% |
| 400-700 | 94-99.8% |
| 700-1600 or 4000 | 0.1-2% |

Alternatively, according to one or more embodiments, the table below provides approximate percentage ranges of irradiance within different wavebands for VL+UVA1 spectral output for the system and method disclosed herein:

| Waveband (nm) | Percentage Range |
|---|---|
| below 370 | less than 0.0001% |
| 370-400 | 0.01-5% |
| 400-700 | 93-99.98 |
| 700-1600 or 4000 | 0.01-2% |

According to one or more embodiments, total irradiance for the range of 370 nm-700 nm may be, for example, from about 45-250 mW/cm$^2$ or may be, for example, from about 40-500 mW/cm$^2$.

EXAMPLE

Embodiments disclosed herein will now be described in more detail by way of an example thereof. It should be noted however that the disclosure is not limited to this example.

Figure 3:
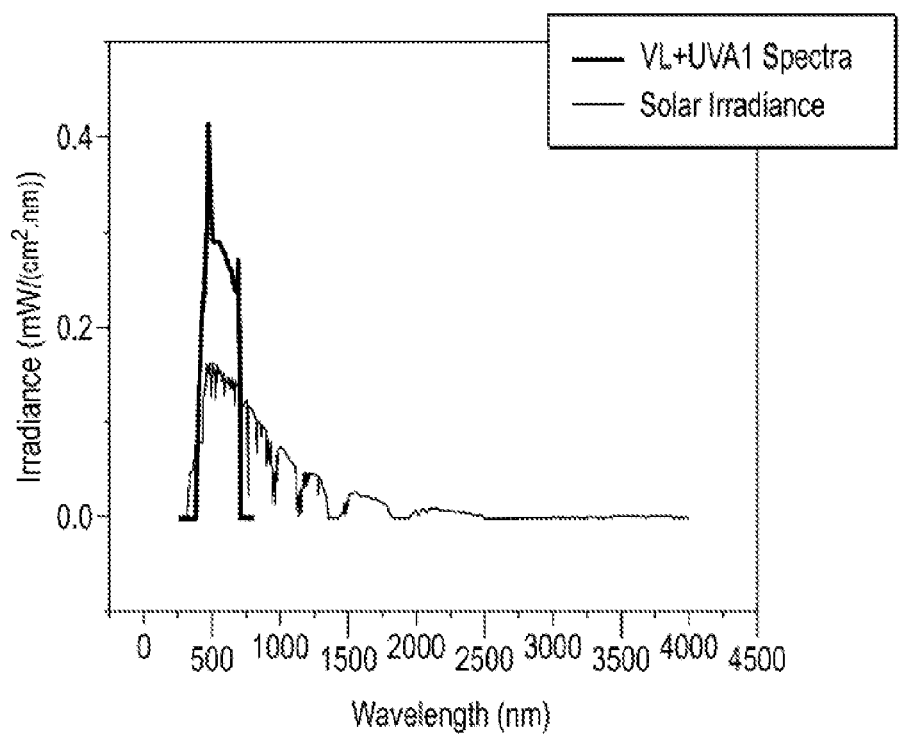
FIG. 3 is a graph of irradiance as a function of wavelength for the customized VL+UVA1 spectral output used in the system and method herein as compared with solar irradiance.

A study was undertaken using the system and method described above to determine the biologic effects of VL+UVA1 on pigmentation and erythema. In this study, approved by the Henry Ford Hospital Institutional Review Board (IRB #11927), ten healthy adult subjects with Fitzpatrick skin phenotypes I-III (light skin) were enrolled. Informed consent was obtained from all subjects, and all guidelines from the Declaration of Helsinki were followed. Subjects using photosensitizing medications or those with a history of skin cancer, photodermatoses, pigmentary disorders (other than postinflammatory hyperpigmentation) as well as those who were active tanners, pregnant, or lactating were excluded. On day 0, each subject's lower back was exposed to a VL+UVA1 dose of 480 J/cm$^2$. An irradiance of approximately 86 mW/cm$^2$ was used, which is less than a factor of 2 compared to that of sunlight allowing for close simulation of outdoor sun exposure. The VL+UVA1 spectra used in the study compared with solar irradiance (American Society of Testing and Materials standard) is illustrated in the graph of FIG. 3.

Assessments for erythema were performed immediately after, at 24 hours, and 7 days after irradiation. Clinical assessments included polarized photography and Investigator's Global Assessment (IGA) Scores for Erythema, listed in the table below:

| IGA | Description |
| --- | --- |
| 0 | Clear of erythema |
| 1 | Almost clear of erythema |
| 2 | Mild, but noticeable erythema |
| 3 | Moderate erythema (pink in quality), no sharp borders |
| 4 | Severe erythema (dark pink in quality), sharp borders |
| 5 | Very severe erythema (very dark pink, almost red in quality) |

A single trained rater performed IGA scoring for all subjects at all visits. Objective instrumental assessments were performed with colorimetry (a*) and diffuse reflectance spectroscopy (DRS) (to assess oxyhemoglobin). An increase in erythema would result in an increase in a* and oxyhemoglobin concentration. Repeated measures analysis of variance was performed to compare the a* and oxyhemoglobin concentration among subjects' baseline non-irradiated skin and VL+UVA1 irradiated sites at all time points (immediately after, at 24 hours, and 7 days after irradiation), Those with p-values<0.05 were considered statistically significant. All analyses were performed using OriginPro software (Version 9.1.0, OriginLab Corporation, Northampton, MA).

Figure 4:
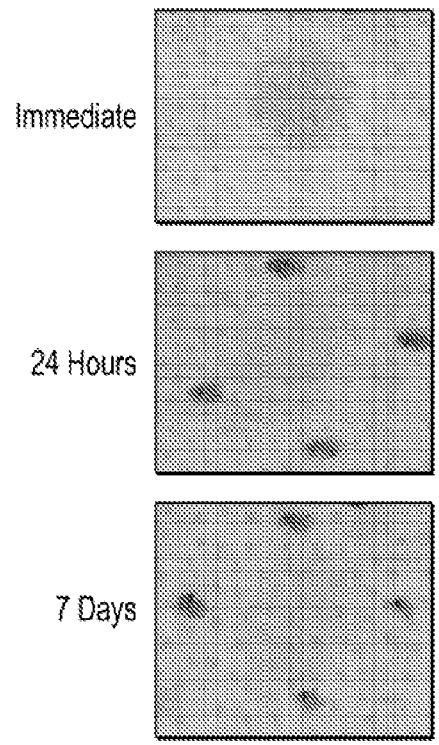
FIG. 4 shows representative cross-polarized photographs of a subject's back following exposure to the customized VL+UVA1 irradiation according to one or more embodiments.
Figure 5:
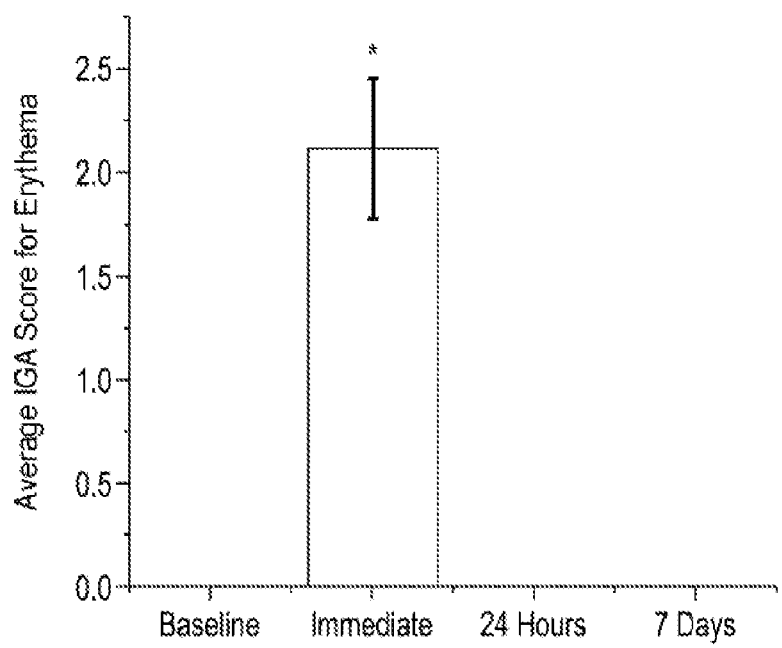
FIG. 5 is a graph of average Investigator's Global Assessment (IGA) scores for erythema following exposure to the customized VL+UVA1 irradiation (statistical significance at immediately after irradiation time point)
Figure 6:
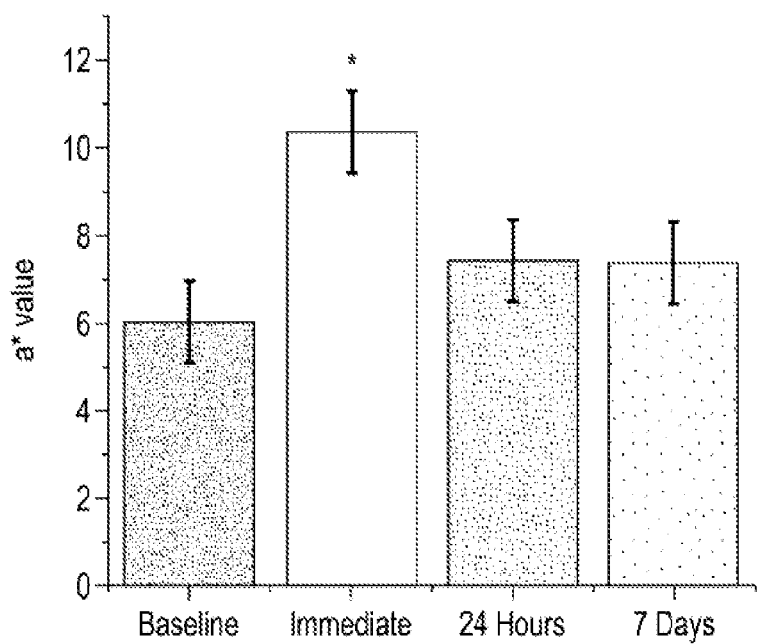
FIG. 6 is a graph of colorimetry measured a* (statistical significance at immediately after irradiation time point) value at various time points following exposure to the customized VL+UVA1 irradiation.
Figure 7:
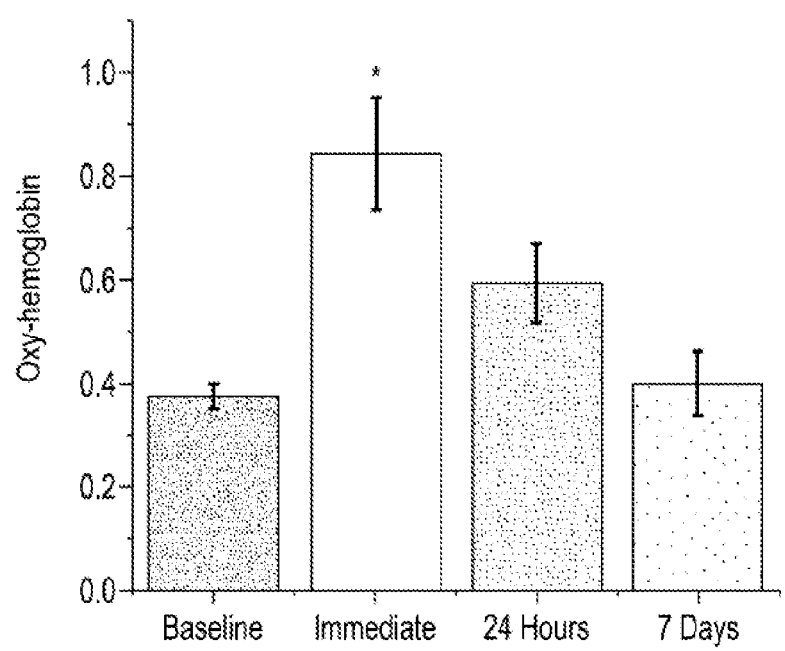
FIG. 7 is a graph of diffuse reflectance spectroscopy (DRS)-measured oxyhemoglobin at various time points following exposure to the customized VL+UVA1 irradiation (statistical significance at immediately after irradiation time point).

All 10 subjects had an erythema response immediately after VL+UVA1 irradiation as illustrated in FIG. 4. The graphs of FIGS. 5, 6 and 7 show erythema assessments via IGA scores for erythema, colorimetry-measured a*, and DRS-measured oxyhemoglobin, respectively, at various time points after irradiation. Both colorimetry and DRS non-invasively quantify changes in pigmentation and erythema by collecting the reflectance spectra. While colorimetry expresses the output in terms of L* (lightness to darkness), a* (green to red), and b* (blue to yellow) color parameters, DRS calculates the concentration of melanin, oxy- and de-oxyhemoglobin, and scattering. For each assessment technique, there was a statistically significant increase in erythema immediately after irradiation compared to the subjects' baseline non-irradiated skin. Clinical erythema completely resolved within 24 hours (FIG. 5); however, some residual erythema was identified via colorimetry and DRS (FIGS. 6 and 7, respectively) 24 hours after irradiation.

The results demonstrated that VL+UVA1 can induce biologic effects, in this case in light-skinned individuals. Clinically perceptible erythema with VL+UVA1 is a novel finding since the erythemogenic spectrum of sunlight has previously primarily been attributed to ultraviolet B (UVB) and short wavelength ultraviolet A (320-340 nm).

Per United States Food and Drug Administration recommendations, the wavelength range of 340-400 nm has been suggested to have a corresponding percent erythemal contribution of 3-6%. This is commensurate with the percentage composition of solar ultraviolet radiation (American Society for Testing and Materials standard, 2008 ASTM G173-03 Reference Spectra). For example, during 30 minutes of outdoor sun exposure, an individual will receive approximately 250 mJ/cm$^2$ of UVB dose and approximately 8 J/cm$^2$ of UVA (approximately 6.5 J/cm$^2$ of which is from UVA1).

Thus, of the total UV dose (8.250 J/cm$^2$), approximately 3% (250 mJ/cm$^2$) is from UVB and remainder 97% (8 J/cm$^2$) is from UVA (with approximately 80% contribution from UVA1). As such, it might seem that UVB dose required to induce any damage is much lower compared to UVA, but interestingly both of these doses will be acquired within the same time period. The corresponding VL+UVA1 dose acquired within 30 minutes (approximately 80 J/cm$^2$) will be an order of magnitude greater compared to total UV dose (8.250 J/cm$^2$), and more than two orders of magnitude greater compared to corresponding UVB dose (250 mJ/cm$^2$).

The VL+UVA1 dose used herein, 480 J/cm$^2$, corresponds to approximately 3 hours of outdoor sun exposure. This duration of sun exposure is very relevant to those who work outdoors or spend time in the sun. Thus, this waveband has the potential to cause erythema even after application of broad-spectrum sunscreen since currently available products on the market do not offer protection in this domain. These results emphasize the need for protection against this part of the solar spectra.

In the United States, any sunscreen that provides greater than 90% of its protection below 370 nm (which is a part of ultraviolet A1) is allowed to claim broad-spectrum photoprotection. Previously, the erythemogenic spectrum of sunlight had primarily been attributed to ultraviolet B and short wavelength ultraviolet A (320-340 nm). However, the system and method disclosed herein have demonstrated that wavelengths that were previously considered inert (370 nm and above) are actually biologically active and have a significant role when combined with VL, which is the case when individuals are outdoors. Accordingly, the system and method described herein use the waveband of 370-700 nm for visible light testing protocols instead of 400-700 nm, while remaining consistent with composition of sunlight.

The method discussed herein for monitoring changes in VL+UVA1-induced skin response can be used for testing product efficacy in skin samples treated with photoprotective substances, such as sunscreen. It is time efficient since a single irradiation, with the suggested spectral output, was sufficient to induce a statistically significant response as described above. Testing of photoprotection products or substances that could modify VL+UVA1-induced changes can then be done using the method described herein.

In summary, there are synergistic effects of VL and long wavelength UVA1 on skin conditions and characteristics, such as pigmentation and erythema. This emphasizes the need for development of sunscreens and other methods of providing photoprotection against this part of the solar spectrum. Additionally, optimal conditions to perform in vivo testing of product efficacy against VL+UVA1-induced biologic effects, including the spectral output, irradiance level and assessment time points have been provided. Considering the biologic effects of VL+UVA1, the spectral output of solar simulators used for photoprotection testing should include VL as implemented in the system and method disclosed herein.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A system for testing an effect of light exposure on a skin sample, the system comprising:
a solar simulator arranged to administer a combination of visible light (VL) and long wavelength ultraviolet radiation (UVA1) to the skin sample, the solar simulator including
a light source for generating a light beam; and
a filter combination including an interference filter for receiving the light beam and emitting a VL+UVA1 spectral output having a wavelength range of 370-700 nm with 2.0%-5% UVA1 (370-400 nm) for irradiating the skin sample.

2. The system of claim 1, wherein the filter combination includes a long pass filter.

3. The system of claim 1, wherein a total irradiance of the VL+UVA1 spectral output is between 40-500 mW/cm$^2$.

4. The system of claim 1, wherein the effect on the skin sample includes changes in at least one of pigmentation or erythema.

5. The system of claim 1, wherein the light source includes a xenon arc lamp.

6. A method for testing an effect of light exposure on a skin sample, the method comprising:
providing a solar simulator arranged to administer a combination of visible light (VL) and long wavelength ultraviolet radiation (UVA1) to the skin sample, the solar simulator including a light source for generating a light beam and a filter combination including an interference filter for receiving the light beam and emitting a VL+UVA1 spectral output having a wavelength range of 370-700 nm with 2.0%-5% UVA1 (370-400 nm); and
irradiating the skin sample with the VL+UVA1 spectral output.

7. The method of claim 6, wherein the filter combination includes a long pass filter.

8. The method of claim 6, wherein a total irradiance of the VL+UVA1 spectral output is between 40-500 mW/cm$^2$.

9. The method of claim 6, wherein the effect on the skin sample includes changes in at least one of pigmentation or erythema.

10. The method of claim 6, further comprising treating the skin sample with a photoprotective substance prior to irradiation.

11. The method of claim 6, wherein the light source includes a xenon arc lamp.

* * * * *